United States Patent [19]
Rader et al.

[11] Patent Number: 6,124,251
[45] Date of Patent: Sep. 26, 2000

[54] TOILET BOWL CLEANING TABLET

[75] Inventors: James E. Rader; William K. Mainquist, both of Pleasanton, Calif.

[73] Assignee: The Clorox Company, Oakland, Calif.

[21] Appl. No.: 09/065,073

[22] PCT Filed: Oct. 24, 1996

[86] PCT No.: PCT/US96/17069

§ 371 Date: Jun. 11, 1998

§ 102(e) Date: Jun. 11, 1998

[87] PCT Pub. No.: WO97/15652

PCT Pub. Date: May 1, 1997

Related U.S. Application Data

[60] Provisional application No. 60/005,969, Oct. 27, 1995.

[51] Int. Cl.$^7$ ............................. C11D 7/28; C11D 17/00
[52] U.S. Cl. ................ 510/191; 510/192; 510/381; 510/446; 510/465; 252/187.33; 4/223; 4/227.1; 134/2; 134/42
[58] Field of Search .............................. 510/191, 192, 510/381, 382, 446, 465; 252/187.33; 134/2, 42; 4/223, 227.1

[56] References Cited

U.S. PATENT DOCUMENTS

| | | | |
|---|---|---|---|
| 4,265,847 | 5/1981 | Hunt et al. | 264/122 |
| 4,427,692 | 1/1984 | Girard | 514/390 |
| 4,537,697 | 8/1985 | Girard | 510/192 |
| 4,560,766 | 12/1985 | Girard et al. | 510/224 |
| 4,654,424 | 3/1987 | Girard et al. | 548/320.5 |
| 4,677,130 | 6/1987 | Puzig | 514/389 |
| 5,160,660 | 11/1992 | Ertle et al. | 252/186.34 |
| 5,178,787 | 1/1993 | Hung et al. | 510/192 |
| 5,338,461 | 8/1994 | Jones | 210/755 |
| 5,464,636 | 11/1995 | Hight et al. | 424/661 |
| 5,478,482 | 12/1995 | Jones et al. | 210/753 |
| 5,514,287 | 5/1996 | Jones et al. | 210/753 |
| 5,578,559 | 11/1996 | Dolan | 510/192 |
| 5,648,314 | 7/1997 | Lachocki et al. | 504/151 |
| 5,670,059 | 9/1997 | Jones et al. | 210/753 |
| 5,674,429 | 10/1997 | Lachocki et al. | 252/186.28 |
| 5,750,061 | 5/1998 | Farina et al. | 264/117 |
| 5,756,440 | 5/1998 | Watanabe et al. | 510/191 |
| 5,780,641 | 7/1998 | Yerushalmi et al. | 548/320.5 |
| 5,851,406 | 12/1998 | Jones et al. | 210/755 |

FOREIGN PATENT DOCUMENTS

96/11167  4/1996  WIPO.

*Primary Examiner*—Lorna M. Douyon
*Attorney, Agent, or Firm*—Burns, Doane, Swecker & Mathis, L.L.P.

[57] ABSTRACT

A cleaning formulation, in tablet form, capable of providing a metered release of cleaning active while immersed in the tank of a toilet. The tablet comprises greater than about 85 to 99 weight percent of a halohydantoin plus about 1 to 15 weight percent of a longevity aid comprising boric acid.

14 Claims, 1 Drawing Sheet

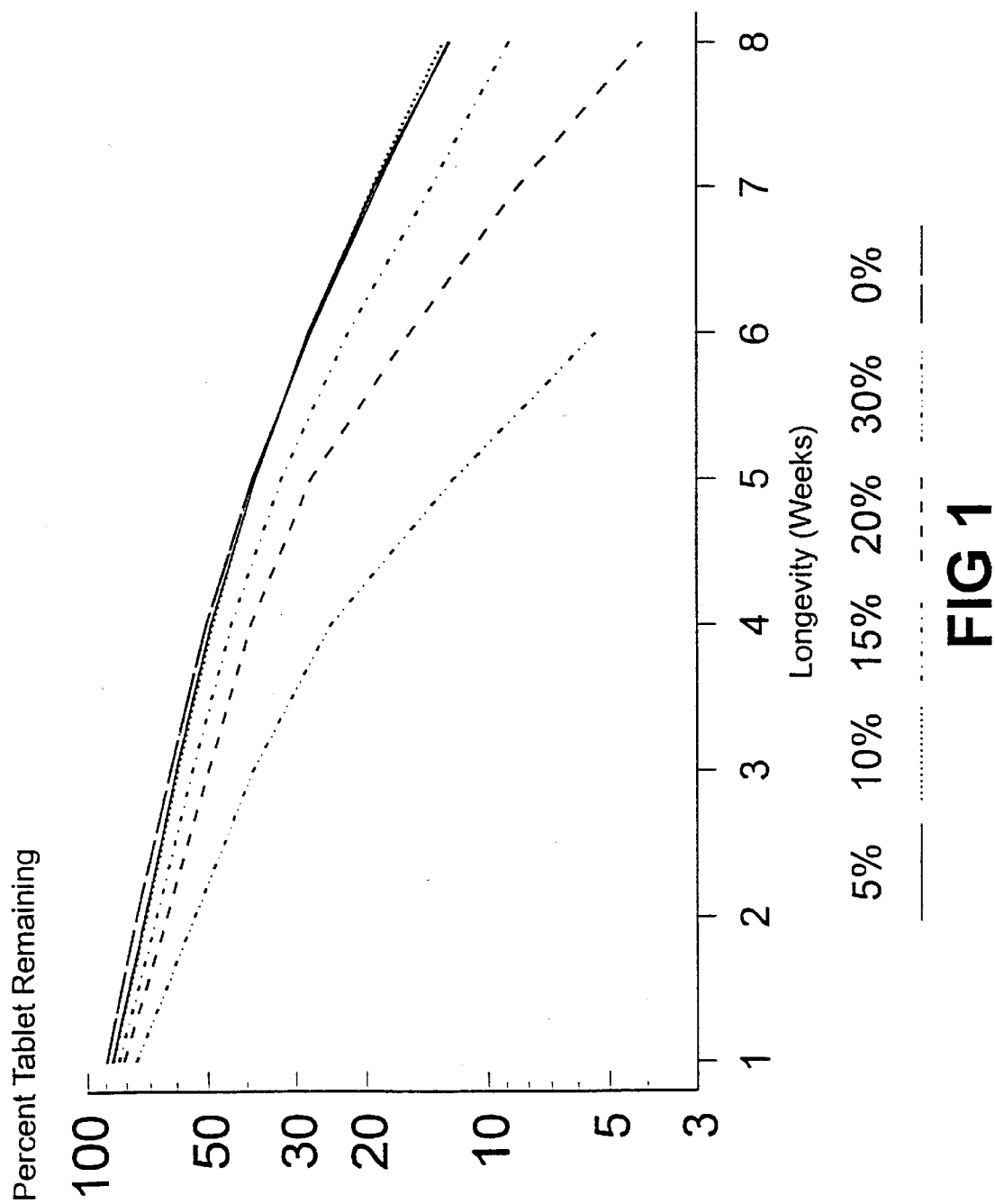

TOILET BOWL CLEANING TABLET

This application claims the benefit of U.S. Provisional Application Ser. No. 60/005,969, filed Oct. 27, 1995.

FIELD OF THE INVENTION

This invention relates to formulations for cleaning toilet bowls, and in particular to an in-tank toilet bowl tablet providing metered release of an active cleaning agent.

BACKGROUND OF THE INVENTION

There are numerous compositions known to the art which can be compressed or tableted, providing a tablet, block or similar article which may be placed in the tank of a toilet and dispense cleaning active over a period of time. Such tablets may consist of, or include various cleaning agents such as bleaches, surfactants, disinfectants, and mixtures thereof. A particularly preferred disinfecting agent is an organic halogen source, and a particularly preferred family of organic halogen sources include halohydantoins. Halohydantoins are particularly preferred for the purpose as they are well suited to tableting and consequent slow release of halogen. Numerous prior art discloses halohydantoin based cleaning tablets for various uses, including U.S. Pat. Nos. 4,427,692; 4,537,697 and 4,560,766, all to Girard.

One of the difficulties associated with toilet bowl cleaning tablets of the art has been to establish a uniform release of active halogen over a commercially feasible term, for example, of two to four months. While dichloro, methylethyl or dimethyl hydantoins can be compressed sufficiently to permit such a long term release, for reasons of formulation efficacy and economics, pure dichloro, methylethyl or dimethyl, or other halohydantoins are not preferred. However sufficient tablet longevity is hindered when such tablets are not pure halohydantoin.

Accordingly, it is an object of the present invention to provide a composite tablet having longevity comparable to a pure halohydantoin tablet.

It is another object of the present invention to provide a composite tablet having cleaning performance comparable to that of a pure halohydantoin tablet.

SUMMARY OF THE INVENTION

The present invention is a cleaning formulation, in tablet form, capable of providing a metered release of cleaning active while immersed in the tank of a toilet.

In one aspect, the invention is directed to a cleaning tablet comprising a halohydantoin and boric acid wherein the halohydantoin comprises greater than about 85% (wt) to about 99% (wt) of the cleaning tablet.

In another aspect, the invention is directed to a method of dispensing uniform amounts of active halogens into a reservoir containing about 6 to 19 liters of water which is periodically flushed and replaced with fresh water which includes the steps of:
 a. placing a cleaning tablet which comprises a halohydantoin and boric acid into said reservoir wherein the halohydantoin comprises greater than about 85% (wt) to about 99% (wt) of the cleaning tablet and wherein active halogen is released from the tablet until the concentration of active halogens in the water is at a desired level of about 0.5 to 5 ppm;
 b. removing the water from the reservoir and replacing said reservoir with fresh water thereby activating the release of the active halogen from the tablet until the concentrate of active halogens in the water reaches said desired level; and
 c. repeating step b until the tablet is essentially completely dissolved, wherein the method is characterized in that the boric acid has a dissolution time of about 0.08 to 0.3 of the total tablet dissolution time.

Preferred halohydantoins are selected from the group consisting of N,N'-dichloro-dimethyl-hydantoin, N-bromo-N-chloro-dimethyl-hydantoin, N,N'-dibromo-dimethyl-hydantoin, 1,4dichloro, 5,5-dialkyl substituted hydantoin, wherein each alkyl group independently has 1 to about 2 carbon atoms, and mixtures thereof.

Preferably, the cleaning tablet has a density of about 1.1 to 1.6 g/cm$^3$. In addition, the cleaning tablet has a superficial surface area to weight ratio of about 1:1 to 2:1 (cm$^2$/g).

BRIEF DESCRIPTION OF THE DRAWING

FIG. 1 is a graph of tablet dissolution rate for various ratios of hydantoin to boric acid.

DETAILED DESCRIPTION OF THE INVENTION

The toilet cleaning tablet or block of the present invention is a generally homogenous solid comprising an active halogen-releasing agent and a longevity aid. The halogen releasing agent releases the halogen when the block is in contact with water. Any such agents known heretofore can be used and it is preferred that such agents are N-halogenated organic compounds, including N,N'-dichloro-dimethyl-hydantoin, N-bromo-N-chloro-dimethyl-hydantoin, N,N'-dibromo-dimethyl-hydantoin. In the present invention, dialkyl substituted hydantoins and especially 1,4dihalo, 5,5-dialkyl substituted hydantoins, are preferred. Preferred is a mixture of bromochloro dimethyl hydantoin (BCDMH), dichloro dimethyl hydantoin (DCDMH), and dichloro methyl ethyl hydantoin (DCMEH). For tableting purposes, DCDMH is preferred as it provides the longest residence time. These halohydantoins are available from Lonza Chemical, Fairlawn, N.J. Preferably the halohydantoins comprise greater than about 85% (wt) to about 99% (wt) of the cleaning block, preferably about 90% (wt) to about 99% (wt), with the remainder comprising boric acid. Preferred tablets can comprise from about 5% (wt) to less than 15% (wt), preferably from about 7.5% (wt) to about 12.5% (wt), and more preferably from about 8% (wt) to about 12% (wt) of the boric acid.

It is known that solid halo-5,5-dialkyl substituted hydantoins dissolve slowly in water. Surprisingly, it was discovered that if a quantity of a boric acid longevity aid was added to the hydantoin mixture within a range of between about 5 and 10% based on the weight of the toilet cleaning block, and if the block was prepared such that it had a density falling within a particular range, namely 1.1 to 1.6 g/cm$^3$ and also if the ratio of superficial surface area (cm$^2$) to weight (grams) fell within a certain range, namely about 1:1 (cm$^2$/g) to 2:1 (cm$^2$/g), the toilet cleaning block would release a controlled, substantially constant amount of halogen disinfecting agent within the range of 0.5–5 ppm over a period of 2 to about 4 months of constant contact with water. The tablet longevity aid must be water soluble, chemically inert, i.e. will have no effect on the solubility of the halohydantoin or halohydantoin mixture, and will completely dissolve in a much shorter time period than the halohydantoin. Preferably, the dissolution time for the longevity aid should be approximately 0.08 to 0.3, more preferably 0.1 to 0.15, of the dissolution time for the overall or total tablet. Stated alternatively, the longevity aid should completely dissolve in approximately 1–4 weeks, preferably 2–3 weeks, for a hydantoin tablet having an approximately 4 month longevity. Optionally compatible adjuncts such as colorants such as dyes, surfactants antimicrobial agents and fragrances may be added to the formulation subject only to the limitation that such adjuncts have substantially no effect on tablet dissolution rate. Although adjuncts can be included, preferred embodiments include tablets that consist essentially of the halohydantoin and basic boric acid.

The block will deliver a constant, uniform efficacious level of active halogen (0.5 to 5 ppm) for about 1000–2000 flushes with water having a temperature of about 50° to 70° F. (10° to 21° C.) and typically about 57° F. (13.9° C.) and will be completely dissolved at the end of its useful life, leaving no residue in the tank. A tank will typically hold about 3.5 gallons (about 13.2 liters) of water, although tank sizes vary, they typically have a capacity that ranges from about 6 to 19 liters. For household applications, the tablet preferably has a mass of at least about 25 grams and more preferably about 50–100 grams.

An important relationship between tablet surface area and tablet volume has been discovered. It has been found that with respect to dissolution of substantially pure halohydantoin tablets, there is a "superficial" surface area which is defined by the exterior topography of the tablet and does not include the interior surface area of the tablet. By "superficial" surface area is meant the geometric or exterior surface of the tablet and not its true surface area. For instance, if the tablet is cube-shaped, then the superficial surface area is calculated as $6 \times s_2$, where s is the length of one side of the cube. It is the ratio of tablet superficial surface area ($cm^2$) to tablet weight (grams) which is important in tablet longevity. The lower the ratio the greater the longevity, and the higher the ratio the shorter the longevity. It has been experimentally determined that a preferred ratio be between about 1:2 to 2:1 ($cm^2/g$) and more preferably about 1.2:1 to 1.3:1 ($cm^2/g$). Without intending to be bound by theory, it is the thought that when a halohydantoin tablet is exposed to water the tablet tends to "cement" together due to water of hydration and hydrogen bonding between particles of the organic bleach. Thus, when exposed to water the halohydantoin forms a matrix that dictates the superficial surface area.

The toilet cleaning tablet of the present invention is prepared by dry mixing the hydantoin and the boric acid, preferably in finely divided form, and an optional internal mold lubricant in the absence of added water. Any adjunct materials are also added to the blend. An external lubricant may be used in the manufacturing process to help release the block from the mold. Any type of mixer such as a twin-shell, ribbon blender or similar type of mixer that is designed to provide a homogeneous admixture can be used. The particle size of the halohydantoin is preferably in the range of 10 to 60 US mesh and that of the boric acid is preferably in the range of 8 to 100 US mesh. The admixture is then transferred to the mold of a press, and pressure is applied sufficient to provide the desired density and effective surface area/weight ratio. The resultant mixture is a coherent solid which is resistant to internal water penetration and has a crush fracturing strength of about 25 to 100 pounds, preferably about 50 to 80 pounds. The strength was measured using an AMETEK force gauge testing device manufactured by the AMETEK Corporation. In order to obtain the desired properties, the pressure will vary depending on the particular chemicals employed and the particle sizes of the particulates.

EXPERIMENTAL

Without being bound to any particular theory, it has been demonstrated that adding up to about 10% boric acid is feasible without affecting the internal matrix structure that occurs when using 100% halohydantoin. The data also suggests that it may be feasible to use up to almost 15% boric acid. The more soluble boric acid will rapidly dissolve from the tablet leaving a remaining "matrix" of the halohydantoin. The result is that the dissolution behavior of the preferred composite tablet is very similar to that of a pure halohydantoin tablet due to similar matrices, yielding similar superficial surface to volume ratios.

As shown in FIG. 1 and in Table 1 below, a 15% boric acid tablet results in a loss of about 6 to 10% longevity, due to the different superficial surface area to weight ratios versus the control (100% halohydantoin). If the boric acid is increased beyond 15% the kinetics of tablet dissolution can be shown to markedly shorten tablet longevity. FIG. 1 is a graph showing the log of percentage tablet remaining versus time (weeks) for two formulations of the present invention (5% and 10% boric acid) three formulations outside the present invention (15, 20 and 30% boric acid) and a 0% boric acid control. In each case, the tablet comprises halohydantoin plus the indicated level of boric acid. The tablets had a superficial surface area to weight ratio of about 1.25:1 ($cm^2/g$). The data presented graphically in FIG. 1 is shown in Table 1 below.

TABLE 1

PERCENTAGE TABLET REMAINING

| Tablet Composition | Time (Weeks) | | | | |
|---|---|---|---|---|---|
| | 1 | 2 | 3 | 4 | 5 |
| A | 86.5 | 71.8 | 59.7 | 48.9 | 37.7 |
| B | 85.9 | 71.1 | 59.0 | 48.4 | 37.8 |
| C | 83.4 | 67.1 | 54.4 | 43.5 | 32.4 |
| D | 81.0 | 63.3 | 49.7 | 38.8 | 27.3 |
| E | 75.8 | 53.9 | 38.4 | 24.4 | 12.1 |
| F | 89.5 | 75.3 | 61.9 | 50.3 | 38.4 |

A = 5% Boric Acid
B = 10% Boric Acid
C = 15% Boric Acid
D = 20% Boric Acid
E = 30% Boric Acid
F = 0% Boric Acid The data from Table 1 above were obtained using the following protocol. Tablets each weighing 70 grams were compressed from appropriate amounts of halohydantoin and boric acid, on a Carver hand press using conventional tablet tooling consisting of a die and an upper and lower punch. The resulting tablets measured about 5.0 cm in diameter and about 2.2 cm in height. The experimental tablets were placed in toilet tanks and flushed three to five times daily. The water temperature was maintained at about 70° (21° C.) to 75° F. (24° C.) for the duration of the test. The tablets were checked daily for weight loss, which data was used to evaluate the longevity of the tablets.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as defined by the following claims.

What is claimed is:

1. A cleaning tablet consisting of a halohydantoin and boric acid wherein the boric acid is present in amounts from 7.5% wt to 15% wt of the cleaning tablet and wherein the tablet has a density of about 1.1 to 1.6 g/cm$^3$ and the tablet has a superficial surface area to weight ratio of about 1:1 to 2:1 cm$^2$/g.

2. The cleaning tablet of claim 1 wherein the halohydantoin is selected from the group consisting of N,N'-dichloro-dimethyl-hydantoin, N-bromo-N-chloro-dimethyl-hydantoin, N,N'-dibromo-dimethyl-hydantoin, 1,4dichloro, 5,5-dialkyl substituted hydantoin, wherein each alkyl group independently has 1 to about 2 carbon atoms, and mixtures thereof.

3. The cleaning tablet of claim 1 wherein the boric acid is present in amounts from 10% wt to 15% wt of the cleaning tablet.

4. The cleaning tablet of claim 1 wherein the tablet has a mass of at least 25 grams.

5. A method of dispensing uniform amounts of active halogens into a reservoir containing about 6 to 19 liters of water which is periodically flushed and replaced with fresh water which comprises the steps of:
   a. placing a cleaning tablet which consists of a halohydantoin and boric acid into said reservoir wherein the boric acid is present in amounts from 7.5% wt to 15% wt of the cleaning tablet and wherein active halogen is released from the tablet until the concentration of active halogens in the water is at a desired level of about 0.5 to 5 ppm wherein the tablet has a density of about 1.1 to 1.6 g/cm$^3$ and the tablet has a superficial surface area to weight ratio of about 1:1 to 2:1 cm$^2$/g;
   b. removing the water from the reservoir and replacing said reservoir with fresh water thereby activating the release of the active halogen from the tablet until the concentrate of active halogens in the water reaches said desired level; and
   c. repeating step b until the tablet is essentially completely dissolved, wherein the method is characterized in that the boric acid has a dissolution time of about 0.08 to 0.3 of the dissolution time of the total tablet, wherein said method is characterized by being able to provide said desired level of active halogens when step b is repeated between 1,000 to 2,000 times and when the water temperature is maintained at about 10° C. to 21° C.

6. The method of claim 5 wherein the boric acid is present in amounts from 10% wt to 15% wt of the tablet.

7. The method of claim 5 wherein the tablet has a mass of at least about 25 grams.

8. A cleaning tablet consisting of a halohydantoin, boric acid and a compatible adjunct that is selected from the group consisting of colorants, surfactant, antimicrobial agents, and fragrances wherein the halohydantoin is greater than 85% wt, the boric acid is present in amounts from 7.5% wt to 15% wt of the cleaning tablet and wherein the tablet has a density of about 1.1 to 1.6 g/cm$^3$ and the tablet has a superficial surface area to weight ratio of about 1:1 to 2:1 cm$^2$/g.

9. The cleaning tablet of claim 8 wherein the halohydantoin is selected from the group consisting of N,N'-dichloro-dimethyl-hydantoin, N-bromo-N-chloro-dimethyl-hydantoin, N,N'-dibromo-dimethyl-hydantoin, 1,4dichloro, 5,5-dialkyl substituted hydantoin, wherein each alkyl group independently has 1 to about 2 carbon atoms, and mixtures thereof.

10. The cleaning tablet of claim 8 wherein the boric acid is present in amounts from 10% wt to 15% wt of the cleaning tablet.

11. The cleaning tablet of claim 8 wherein the tablet has a superficial surface area to weight ratio of about 1.2:1 to 1.3:1 cm$^2$/g.

12. A method of dispensing uniform amounts of active halogens into a reservoir containing about 6 to 19 liters of water which is periodically flushed and replaced with fresh water which comprises the steps of:
   a. placing a cleaning tablet which consists of a halohydantoin, boric acid, and a compatible adjunct that is selected from the group consisting of colorants, surfactant, antimicrobial agents, and fragrances into said reservoir wherein the halohydantoin is greater than 85% wt, the boric acid is present in amounts from 7.5% wt to 15% wt of the cleaning tablet and wherein active halogen is released from the tablet until the concentration of active halogens in the water is at a desired level of about 0.5 to 5 ppm wherein the tablet has a density of about 1.1 to 1.6 g/cm$^3$ and the tablet has a superficial surface area to weight ratio of about 1:1 to 2:1 cm$^2$/g;
   b. removing the water from the reservoir and replacing said reservoir with fresh water thereby activating the release of the active halogen from the tablet until the concentrate of active halogens in the water reaches said desired level; and
   c. repeating step b until the tablet is essentially completely dissolved, wherein the method is characterized in that the boric acid has a dissolution time of about 0.08 to 0.3 of the dissolution time of the total tablet, wherein said method is characterized by being able to provide said desired level of active halogens when step b is repeated between 1,000 to 2,000 times and when the water temperature is maintained at about 10° C. to 21° C.

13. The method of claim 12 wherein the boric acid is present in amounts from 10% to 15% wt of the tablet.

14. The method of claim 12 wherein the tablet has a mass of at least about 25 grams.

* * * * *